(12) United States Patent
Sadhu

(10) Patent No.: US 9,571,297 B2
(45) Date of Patent: Feb. 14, 2017

(54) SYSTEM AND METHOD FOR COMMUNICATION BETWEEN FUNCTIONAL DEVICE AND HOME AUTOMATION

(71) Applicant: Rajendra Padma Sadhu, Somerset, NJ (US)

(72) Inventor: Rajendra Padma Sadhu, Somerset, NJ (US)

( * ) Notice: Subject to any disclaimer, the term of this patent is extended or adjusted under 35 U.S.C. 154(b) by 0 days.

(21) Appl. No.: 14/736,607

(22) Filed: Jun. 11, 2015

(65) Prior Publication Data

US 2015/0280937 A1 Oct. 1, 2015

Related U.S. Application Data

(63) Continuation of application No. 13/361,982, filed on Jan. 31, 2012, now Pat. No. 9,083,546.

(51) Int. Cl.
*H04L 12/28* (2006.01)
*H04L 29/08* (2006.01)
(Continued)

(52) U.S. Cl.
CPC ......... *H04L 12/2825* (2013.01); *A61B 5/0022* (2013.01); *A61B 5/0205* (2013.01); *A61B 5/1112* (2013.01); *A61B 5/1176* (2013.01); *A61B 5/7465* (2013.01); *G06F 3/04842* (2013.01); *G06K 9/00832* (2013.01); *G06K 9/00885* (2013.01); *H04L 12/2827* (2013.01); *A61B 5/01* (2013.01); *A61B 5/021* (2013.01); *A61B 5/02438* (2013.01); *A61B 5/0404* (2013.01); *A61B 5/0816* (2013.01); *A61B 5/14532* (2013.01); *G06K 2009/00939* (2013.01); *H04L 67/12* (2013.01); *H04L 2012/40273* (2013.01); *H04W 4/046* (2013.01); *H04W 84/005* (2013.01)

(58) Field of Classification Search
CPC ............ G06F 3/04842; H04L 12/2827; H04L 12/2825; H04L 2012/40273; H04L 67/12; G06K 9/00885; G06K 2009/00939; G06K 9/00832; A61B 5/1176; A61B 5/7465; A61B 5/0022; A61B 5/01; A61B 5/021; A61B 5/14532; H04W 4/046; H04W 84/005
See application file for complete search history.

(56) References Cited

U.S. PATENT DOCUMENTS

2002/0066029 A1* 5/2002 Yi .................. H04L 63/0272
726/15
2002/0156899 A1* 10/2002 Sekiguchi ............ H04L 12/10
709/227

(Continued)

*Primary Examiner* — Dinh P Nguyen
(74) *Attorney, Agent, or Firm* — D'Ambrosio & Menon, PLLC; Usha Menon

(57) ABSTRACT

A functional device is disclosed that can collect and process data/information/parameter values from one or more sensors and compares the same with one or more predefined/threshold value to suggest one or more actions and/or generate alerts/messages/suggestions to be performed by one or a combination of remote system, wearer, home automation network, healthcare provider, doctor, caretaker, among other stakeholders. Communication between the functional device, home automation server and a computational server that stores the data is also disclosed.

6 Claims, 8 Drawing Sheets

(51) Int. Cl.
*H04L 12/40* (2006.01)
*H04W 4/04* (2009.01)
*H04W 84/00* (2009.01)
*A61B 5/00* (2006.01)
*A61B 5/0205* (2006.01)
*A61B 5/11* (2006.01)
*A61B 5/01* (2006.01)
*A61B 5/021* (2006.01)
*A61B 5/024* (2006.01)
*A61B 5/0404* (2006.01)
*A61B 5/08* (2006.01)
*A61B 5/145* (2006.01)
*G06F 3/0484* (2013.01)
*G06K 9/00* (2006.01)
*A61B 5/117* (2016.01)

(56) References Cited

U.S. PATENT DOCUMENTS

| | | | |
|---|---|---|---|
| 2006/0271695 A1* | 11/2006 | Lavian | G06F 21/552 |
| | | | 709/229 |
| 2007/0090944 A1* | 4/2007 | Du Breuil | G08B 25/009 |
| | | | 340/531 |
| 2010/0017759 A1 | 1/2010 | Birnbaum et al. | |
| 2010/0234692 A1* | 9/2010 | Kuo | A61B 5/00 |
| | | | 600/300 |
| 2010/0235454 A1 | 9/2010 | Holden et al. | |
| 2013/0048809 A1 | 2/2013 | Jacobson | |

\* cited by examiner

SYSTEM AND METHOD FOR COMMUNICATION BETWEEN FUNCTIONAL DEVICE AND HOME AUTOMATION

CROSS REFERENCE OF RELATED APPLICATION

This is a Continuation-In-Part application of a non-provisional application having an application Ser. No. 13/361,982, the contents of which are hereby incorporated by reference in their entirety.

BACKGROUND OF THE INVENTION

The background description is not an admission that any of the information provided herein is prior art or relevant to exemplary embodiments described herein, or that any publication specifically or implicitly referenced is prior art.

Generally, motor vehicles include a variety of electronic devices for convenience and safety. Among them few cars and other vehicles provide automatic climate system to maintain a set temperature for the driver and passenger and also provide an automatic lighting system to illuminate interior of the vehicle and control external lights of the vehicle. Even many convenience features such as seat adjustments, steering wheel adjustments, automatic mirrors, and the like provide additional convenience for drivers and passengers. Also other features such as intelligent airbags are able to discriminate children from adults to prevent deployment for further safety.

However, existing electronic devices that form part of an automobile have limited capabilities in terms of providing health monitoring by means of various sensors and communicating data/information from such sensors to a remote server/repository where the data can be assessed/monitored/processed in real-time. Furthermore, even though few ambulances provide medical assistance, such services/capabilities are not present in normal automobiles/vehicles in general. Furthermore, existing automobiles do not attempt to couple, integrate, and/or optimize performance of vehicles based on user's health monitoring output, user's preferences, vehicle characteristics, user's profile, automobile settings, among other automobile related parameters such as speed, location, among others. Existing systems also do not efficiently enable transmission of such automobile and/or health information to one or more servers for real-time remote assessment thereof for recommendations/health indications to be put forth.

In addition, existing systems/architectures that enable viewing status of and/or controlling home electrical equipment/automation system remotely also have strong limitations. Existing architectures of such home electrical equipment/automation systems do not provide a single interface such as a single device for users to monitor their health conditions in automobiles and transmit health related information to a server/repository, wherein the same interface/device also enables the user to view/process/evaluate status of one or more home automation sensors and control them remotely.

There is therefore a need in the art for a functional device that enables monitoring of health parameters/conditions of a user and also enables remote viewing/monitoring/controlling of home automation sensors/system.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The present disclosure provides a functional device that enables monitoring of health parameters/conditions of a user and also enables remote viewing/monitoring/controlling of home automation sensors/system. The present disclosure further provides systems and methods for enabling communication between an automobile configured functional device and a home automation system, wherein the functional device can be configured to provide a user interface that enables users to view automobile parameters such as speed, tyre pressure, fuel attributes, location, among other like parameters; automobile settings such as seat settings, air conditioner settings, among other like settings/preferences; and health parameters/conditions by means wired/wireless sensors that operatively couple with the user and assess/evaluate/monitor health conditions of the user.

According to one exemplary embodiment, functional device of the present disclosure can be configured to enable an occupant of an automobile to view/determine/manage automobile parameters, automobile settings, and health parameters of either the automobile or the occupant in the automobile, on the interface/display of the device. The device can further be configured to authenticate the user/occupant of the automobile using biometrics, based on which, settings/preferences for the user can, in an instance, be automatically changed/modified. In case of multiple occupants of an automobile, such authentication of a user can enable automatic retrieval of stored settings for the respective occupant and adjustment of the automobile parameters based on the same. According to another embodiment, one or more wired/wireless sensors can be configured to compute health parameters of an occupant of an automobile and transmit the determined/computed parameters, say wirelessly to a central repository/server using secured data transmission mechanisms. In an aspect, the wireless health parameter monitoring sensor can be configured to transmit data/information through existing means including but not limited to radio frequency (RF), Bluetooth, Zigbee, WiFi, among other like means.

According to one exemplary embodiment, functional device of the present disclosure can further be configured to be operatively coupled (directly or indirectly) with a home automation system (HAS), wherein the HAS can include one or more sensors that can be operatively coupled with a home automation gateway (HAG) through wired/wireless means. Such sensors can be configured to capture one or more attributes such as lights, fan, air conditioners, home doors, gas system, garage door, window, security camera, fire, smoke sensors, among other like home applications. Data from such sensors can be communicated with the HAG through known wireless means such as Bluetooth®, Zigbee®, Zwave®, Wireless, wired, or Wi-Fi means, among any other known means.

According to one exemplary embodiment, both the HAS and the functional device can be configured to be operatively coupled with a common or respective servers such as web servers, wherein data/information sent from sensors of the HAS can be transmitted to respective HAS server by HAG, whereas information/content from the functional device, which can include health parameters and/or automobile parameters/settings can be stored in respective health content server. In case a common server is configured, data/information from both the functional device as well as from the HAG can be sent to the common web server. One should appreciate that although the present disclosure has been explained with reference to a web server, any other repository that can store such information/data and enable efficient retrieval of such data is completely within the scope of the present disclosure.

According to another exemplary embodiment, content from HAS and/or functional device can be stored in a web server, wherein a web application can be configured to enable access to the data. Such access can be protected by means of a network security device such as a gateway, firewall, router, intrusion prevention system, and intrusion detection system, among other like devices. Such a web application can be configured to authenticate a user and then enable configured data to be visible to the user, which can be enabled for amendment/modification as per the access/modification rights associated with the user. The application can also be accessed on the functional device and/or on a remote device to enable remote monitoring of health conditions and/or home automation system and controlling of the same. Communication can then also be enabled between a health professional and the user by means of the functional device, wherein the user can communicate through voice, video, or textual means with the health professional and take instructions one or more actions to be performed in view of the health parameters sent by the user through the functional device.

According to another exemplary embodiment, the functional device can directly interface with HAS server through say a mobile virtual private network (MVPN) connection based on the IP address of the HAS server. In another aspect, system of the present disclosure can enable the functional device to send a SMS to the HAS server, based on receipt of which, the HAS server can decode the message and return the response. For instance, in case, on the interface of the functional device, it is determined that the gas sensor indicates the gas being ON, an SMS instructing the HAS server to switch OFF the gas can be sent by the functional device, which can be decrypted by the HAS server and accordingly instructions can be sent to the gas sensor through the HAG to turn off the gas.

According to one exemplary embodiment, the functional device may be a portable device, may be inbuilt in the automobile or can be hanged in the automobile through a suction means and the like. According to one aspect, the proposed system can include a cellular data communication module or a Wi-Fi communication module inbuilt in the functional device for transmitting the plurality of health parameters to a remote health monitoring station over a communication network.

According to one exemplary embodiment, the functional device may automatically issue commands to HAS server when the functional device is within the Wi-Fi or Bluetooth® range of the HAS or HAG to automatically change the status of the sensors like turning the lights on or Fans on etc. these actions can be pre-configured on the device or programmed on need basis.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label. Other objects and advantages of the present invention will become apparent to those skilled in the art upon reading the following detailed description of the preferred embodiments, in conjunction with the accompanying drawings, wherein like reference numerals have been used to designate like elements and wherein.

DETAILED DESCRIPTION

Figure 1:
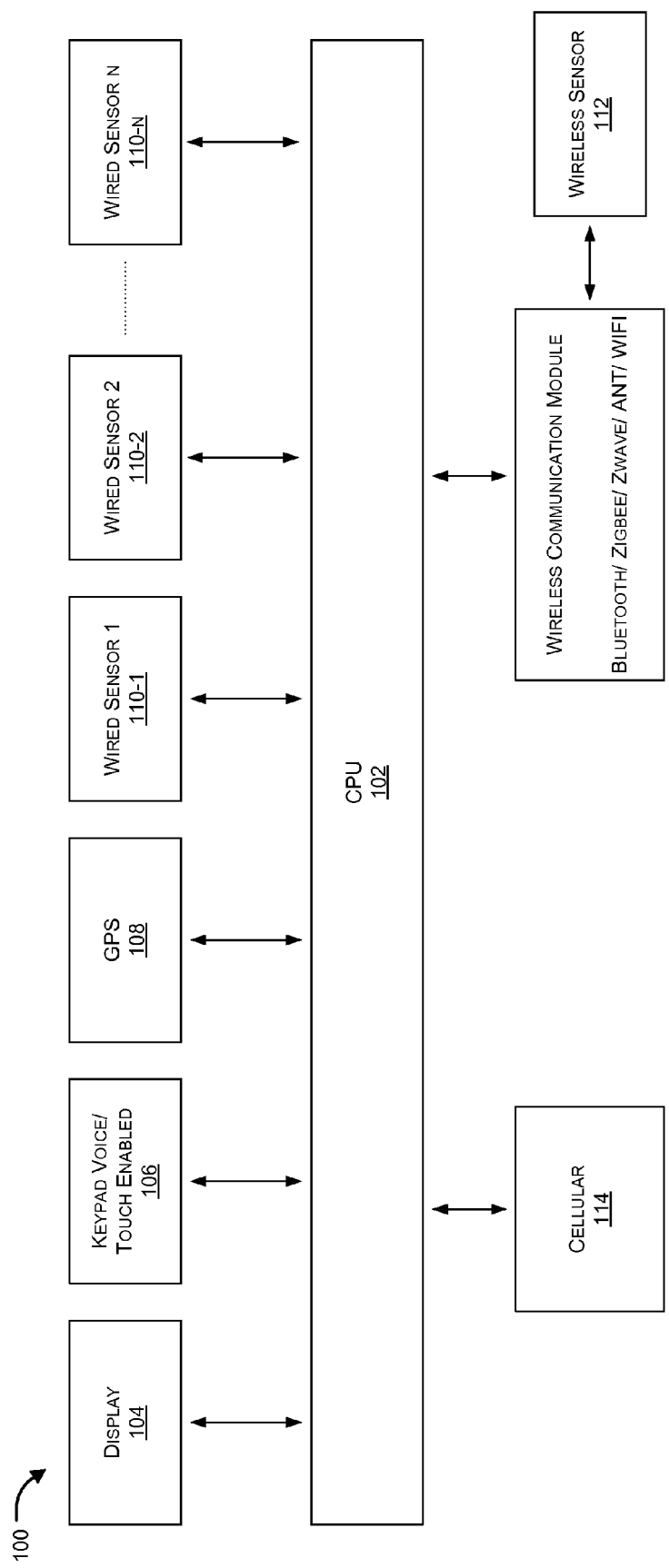
FIG. 1 illustrates an exemplary representation showing constructional details of a functional device in accordance with an embodiment of the present disclosure.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, steps may be performed by a combination of hardware, software, firmware and/or by human operators.

Embodiments of the present invention may be provided as a computer program product, which may include a machine-readable storage medium tangibly embodying thereon instructions, which may be used to program a computer (or other electronic devices) to perform a process. The machine-readable medium may include, but is not limited to, fixed (hard) drives, magnetic tape, floppy diskettes, optical disks, compact disc read-only memories (CD-ROMs), and magneto-optical disks, semiconductor memories, such as ROMs, PROMs, random access memories (RAMs), programmable read-only memories (PROMs), erasable PROMs (EPROMs), electrically erasable PROMs (EEPROMs), flash memory, magnetic or optical cards, or other type of media/machine-readable medium suitable for storing electronic instructions (e.g., computer programming code, such as software or firmware).

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within a single computer) and storage systems containing or having network access to computer program(s) coded in accordance with various methods described herein, and the method steps of the invention could be accomplished by modules, routines, subroutines, or subparts of a computer program product.

If the specification states a component or feature "may", "can", "could", or "might" be included or have a characteristic, that particular component or feature is not required to be included or have the characteristic.

Although the present disclosure has been described with the purpose of using a wearable device such as a watch, band, or like device, for monitoring health conditions and controlling home automation networks, it should be appreciated that the same has been done merely to illustrate the invention in an exemplary manner and any other purpose or function for which the explained structure or configuration can be used, is covered within the scope of the present disclosure.

Exemplary embodiments will now be described more fully hereinafter with reference to the accompanying drawings, in which exemplary embodiments are shown. This invention may, however, be embodied in many different forms and should not be construed as limited to the embodiments set forth herein. These embodiments are provided so that this disclosure will be thorough and complete and will fully convey the scope of the invention to those of ordinary skill in the art. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named.

The present disclosure provides a functional device that enables monitoring of health parameters/conditions of a user or automobile and also enables remote viewing/monitoring/controlling of home automation sensors/system. The present disclosure further provides systems and methods for enabling communication between an automobile configured functional device and a home automation system, wherein the functional device can be configured to provide a user interface that enables users to view automobile parameters such as speed, tire pressure, fuel attributes, location, among other like parameters; automobile settings such as seat settings, air conditioner settings, among other like settings/preferences; and health parameters/conditions by means wired/wireless sensors that operatively couple with the user and assess/evaluate/monitor health conditions of the user.

According to one embodiment, functional device of the present disclosure can be configured to enable an occupant of an automobile to view/determine/manage automobile parameters, automobile settings, and health parameters on the interface/display of the device. The device can further be configured to authenticate the user/occupant of the automobile, based on which, settings/preferences for the user can, in an instance, be automatically changed/modified. In case of multiple occupants of an automobile, such authentication of a user can enable automatic retrieval of stored settings for the respective occupant and adjustment of the automobile parameters based on the same. According to another embodiment, one or more wired/wireless sensors can be configured to compute health parameters of an occupant of an automobile and transmit the determined/computed parameters, say wirelessly to a central repository/server. In an aspect, the wireless health parameter monitoring sensor can be configured to transmit data/information through existing means including but not limited to radio frequency (RF), Bluetooth, Zigbee, WiFi, among other like means.

According to one embodiment, functional device of the present disclosure can further be configured to be operatively coupled (directly or indirectly) with a home automation system (HAS), wherein the HAS can include one or more sensors that can be operatively coupled with a home automation gateway (HAG) through wired/wireless means. Such sensors can be configured to capture one or more attributes such as lights, fan, air conditioners, home doors, gas system, garage door, window, security camera, fire, smoke sensors, among other like home applications. Data from such sensors can be communicated with the HAG through known wireless means such as Bluetooth®, Zigbee®, Zwave®, Wireless, wired, or Wifi means, among any other known means.

According to one embodiment, both the HAS and the functional device can be configured to be operatively coupled with a common or respective servers such as web servers, wherein data/information sent from sensors of the HAS can be transmitted to respective HAS server by HAG, whereas information/content from the functional device, which can include health parameters and/or automobile parameters/settings can be stored in respective health content server. In case a common server is configured, data/information from both the functional device as well as from the HAG can be sent to the common web server. One should appreciate that although the present disclosure has been explained with reference to a web server, any other repository that can store such information/data and enable efficient retrieval of such data is completely within the scope of the present disclosure.

According to another embodiment, content from HAS and/or functional device can be stored in a web server, wherein a web application can be configured to enable access to the data. Such access can be protected by means of a network security device such as a gateway, firewall, router, intrusion prevention system, and intrusion detection system, among other like devices. Such a web application can be configured to authenticate a user and then enable configured data to be visible to the user, which can be enabled for amendment/modification as per the access/modification rights associated with the user. The application can also be accessed on the functional device and/or on a remote device to enable remote monitoring of health conditions and/or home automation system and controlling of the same. Communication can then also be enabled between a health professional and the user by means of the functional device, wherein the user can communicate through voice, video, or textual means with the health professional and take instructions on one or more actions to be performed in view of the health parameters sent by the user through the functional device.

According to another embodiment, the functional device can directly interface with HAS server through say a virtual private network (VPN) connection based on the IP address of the HAS server. In another aspect, system of the present disclosure can enable the functional device to send a SMS to the HAS server, based on receipt of which, the HAS server can decode the message and return the response. For instance, in case, on the interface of the functional device, it is determined that the gas sensor indicates the gas being ON, an SMS instructing the HAS server to switch OFF the gas can be sent by the functional device, which can be decrypted by the HAS server and accordingly instructions can be sent to the gas sensor through the HAG to turn off the gas.

According to one embodiment, the functional device may be a portable device, may be inbuilt in the automobile or can be hanged in the automobile through a suction means and the like. According to one aspect, the proposed system can include a cellular/Wi-Fi data communication module inbuilt in the functional device for transmitting the plurality of health parameters to a remote health monitoring station over a communication network.

According to another embodiment, the present disclosure relates to an inter-exchange data communication system that is configured to remotely monitor sensor information, wherein the system can include a first local area network that is communicatively coupled with one or more health parameter related sensors, a second local area network that is communicatively coupled with one or more home automation system sensors, and a third local area network that is communicatively coupled with a data storage means and a processor, wherein the system can further be configured to enable exchange of information between the first, second and third local area networks using a virtual private network (MVPN) to collectively collect sensor information from first local area network and from second local area network and store the sensor information in data storage means of the third local network, and wherein the system is further configured to enable operation of any of health parameter related sensors and/or home automation system sensors from any local area network.

In an aspect, the first local area network can include a functional device that is communicatively coupled with at least one of said one or more health parameter related sensors that are placed in an automobile. In another aspect, the first local area network can be communicatively coupled with one or more automobile sensors. In yet another aspect, the second local network can include a home automation gateway (HAG) device that can be communicatively coupled with at least one of said one or more home automation system sensors that are placed at predetermined location(s), and wherein the home automation gateway (HAG) device can be operatively coupled with the functional device. In yet another aspect, communication between the first, the second, and the third local area networks can be through a secured channel.

FIG. 1 illustrates an exemplary representation 100 showing constructional details of a functional device in accordance with an embodiment of the present disclosure. As shown, the functional device 100 can include a central processing unit (CPU) 102 that is operatively coupled with a display 104, a keypad or a touch/voice enabled interface 106, a GPS 108, one or more wired sensors 110, and one or more wireless sensors 112 that are coupled with the CPU 102 by means of one or a combination of communication means such as RF (Radio Frequency), Bluetooth®, ZIGBEE®, ZWAVE®, WiFi, among other like means, this will be considered as first local area network.

According to one embodiment, the functional device 100 can further include a cellular means/module 114 inbuilt in the functional device 100 for transmitting plurality of health parameters to a remote health monitoring station over a communication network. In an aspect, sensors 110 and 112 can be configured to retrieve one or more health parameters from the occupant of the vehicle or health of the automobile and either automatically/in real-time or at periodic intervals send such retrieved health parameters to a remote server such as a web server, which can be accessed by one or more health/medical professionals such as doctors and other users/stakeholders that are configured by the occupant to be able to view/analyze and process the health parameter data.

According to another embodiment, display 104 of the functional device 100 can be configured to present, apart from computed health parameter information/data, vehicle/automobile parameters and settings such as status of doors, type pressure, time/date, speed, average, occupants' profile, occupants preference, among other like parameters. GPS 108 on the other hand, can assist in identifying the current location of the occupant/user of the vehicle along with determining the route to the destination. According to one embodiment, the functional device 100 can be portable device, may be inbuilt in the automobile or can be hanged in the automobile through a suction means and the like. Functional device 100 can also include a portable device such as a smart phone/mobile phone that can be detachably coupled with the automobile/vehicle and enable gathering of vehicle status/parameters/settings along with being able to couple one or more health monitoring sensors.

Figure 2:
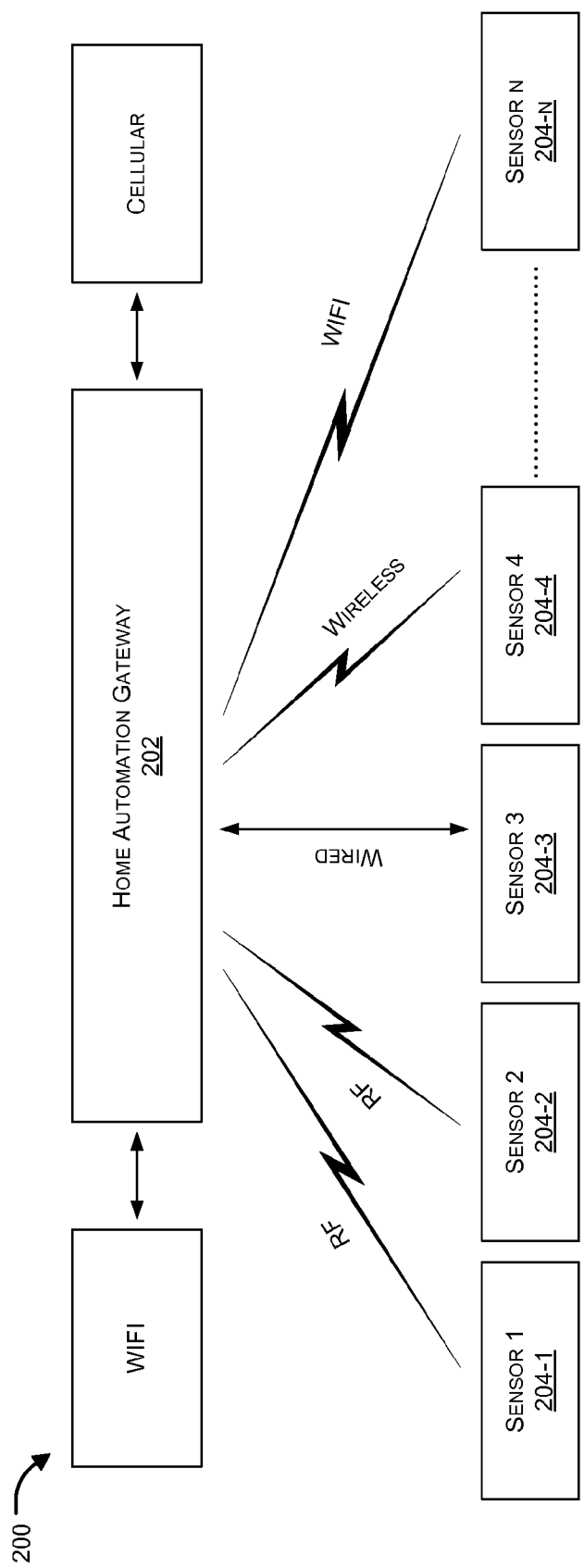
FIG. 2 illustrates an exemplary representation showing constructional details of a home automation system (HAS) in accordance with an embodiment of the present disclosure.

FIG. 2 illustrates exemplary representation showing constructional details of a home automation system (HAS) 200 in accordance with an embodiment of the present disclosure. As shown, the HAS 200 can include a home automation gateway (HAG) 202 that is operatively coupled with one or more home automation sensors 204-1, 204-2, . . . , 204-$n$ (collectively referred to as sensors 204 hereinafter) through one or more wired/wireless means (including but not limited to Wi-Fi, RF, Bluetooth®, ZigBee®, etc.) to gather status information of one or more home automation devices that the sensors 204 are coupled with. This will be considered as second local area network. According to one embodiment, the HAG 202 can be configured to use cellular means to transmit status information of one or more sensors 204 indicating for instance whether the coupled devices are ON or OFF, to a central server/repository. Apart from cellular means, HAG 202 can also be configured to use WiFi means to transmit the gathered information.

According to one embodiment, in view of FIGS. 1 and 2, functional device 100 can be operatively coupled with the HAS 200 by means of a network such as Internet, or through cellular means to enable the functional device 100 to request for status of one or more HAS sensors 204 and display status of the sensors 204 on its display 102. Such display 102 can, for instance, display status of the lights, doors, among other like devices that are operatively coupled with the HAS sensors 204. Functional device 100 can then enable controlling of the HAS sensors 204 and the devices coupled thereto by means of changing the settings of the sensors 204 on the interface of the functional device 100.

Figure 3:
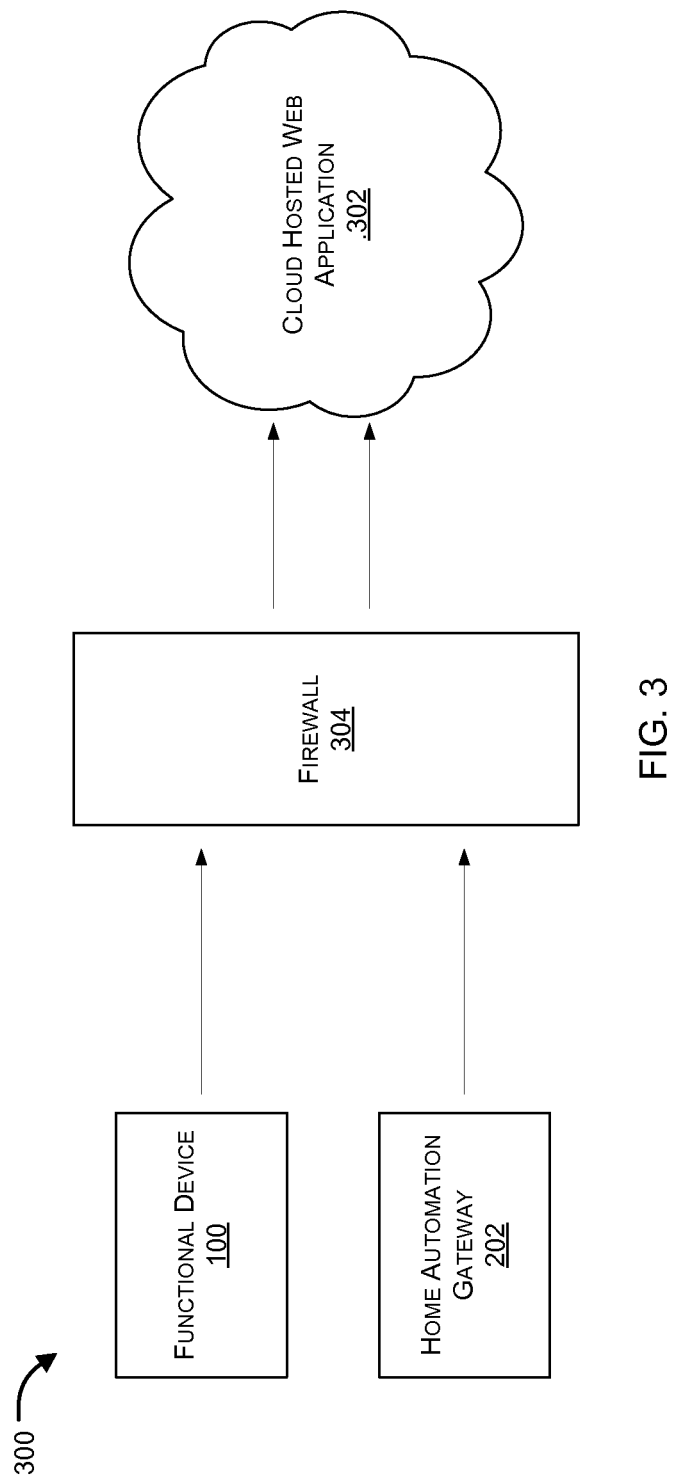
FIG. 3 illustrates an exemplary representation showing access to information/data stored by HAG and functional device in accordance with an embodiment of the present disclosure.

FIG. 3 illustrates an exemplary representation 300 showing access to information/data stored by HAG 202 and functional device 100 in accordance with an embodiment of the present disclosure. As shown, functional device 100 and HAG 202 can be enabled to access a common or respective web servers where data/information generated thereby can be stored and/or accessed/processed/managed. For instance, health parameters generated by means of sensors such as for measuring pulse rate, ECG, blood pressure, body temperature, heart rate, blood sugar, breath rate, and the like, can be stored in real-time in a web server. Similarly, home automation data relating to sensors such as 204 can be stored by the AHG 202 in another or the same web server. Based on such data, a web application 302 can be configured so as to provide an interface to concerned stakeholders such as occupant/user of the automobile, medical professionals, parents, insurance companies among others to view/access and process the data. Such an application 302 can be web-based and accessible on the functional device 100 itself, which can enable the vehicle occupant to review the health records/information, recommendations/suggestions/instructions from the doctor, review reminders, along with also viewing and controlling the HAS sensors 204.

According to one embodiment, functional device 100 and/or the HAG 202 can access the web-application 302 through a network security device 304 such as Firewall, gateway device, IPS, IDS, among other like devices which will be considered as third local area network. According to another embodiment, the web application 302 can be hosted on a cloud based server and accessed by means of a username and password. Each functional device 100 can have an account with the application 302 such that the application 302 can further enable uploading of health parameters in real-time onto the server and further enable the user/occupant of the automobile to configure, through the functional device 100, the data/medical records that are to be viewed, presented, along with inserting comments or adding further medical history/background information.

Figure 4:
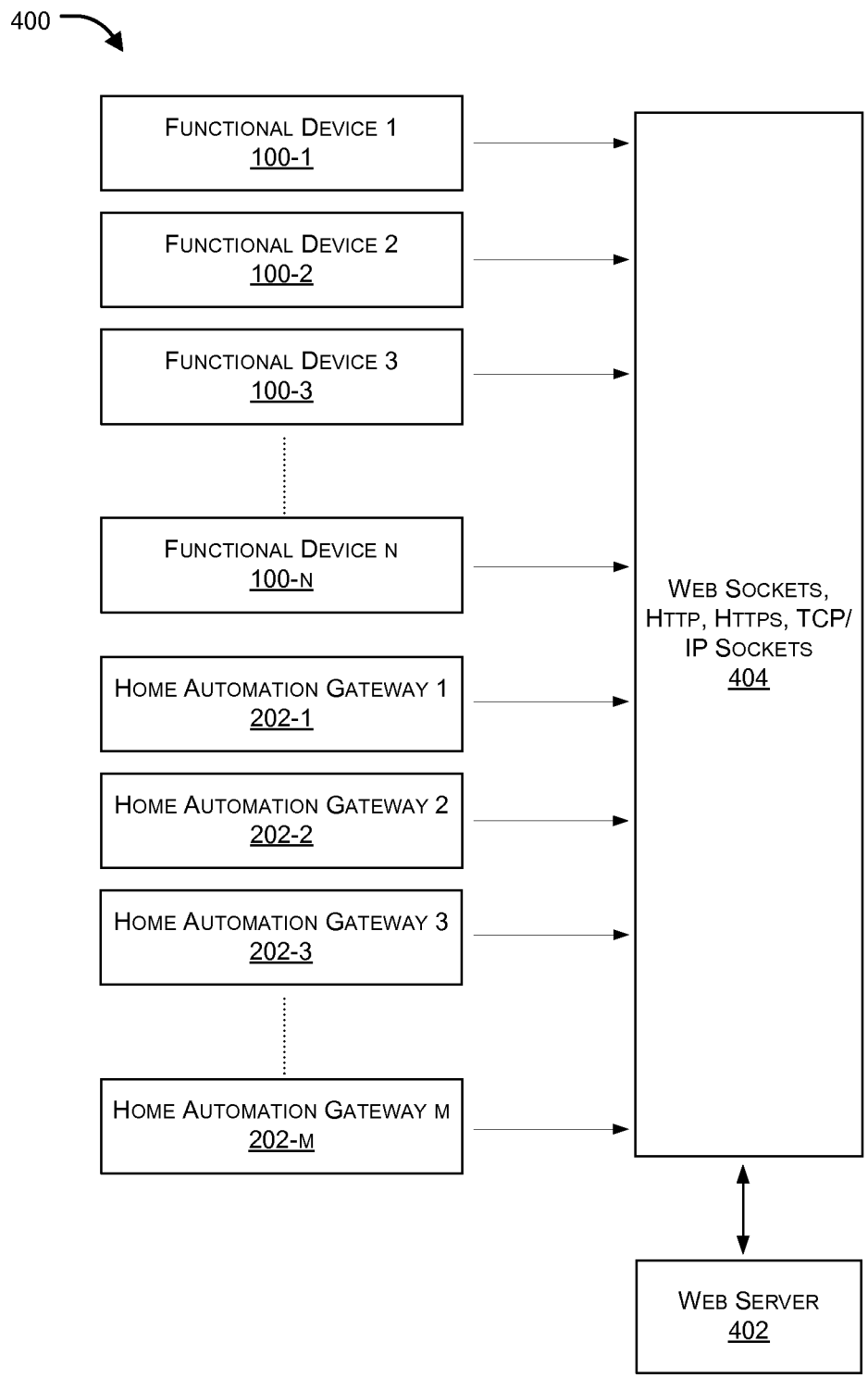
FIG. 4 illustrates another exemplary representation showing access to information/data stored by HAG and functional device in accordance with an embodiment of the present disclosure.

FIG. 4 illustrates another exemplary representation 400 showing access to information/data stored by HAG and functional device in accordance with an embodiment of the present disclosure. As shown, multiple functional devices 100-1, 100-2, . . . , 100-$n$ can be configured to use the same application 302 that can be hosted on a web server 402 that stores medical/health parameters. Each functional device 100 can be configured to have an account with the application 302 such that upon authentication, the device 100 can be allowed to upload health parameters of an occupant of an automobile that the device 100 is associated with. In an aspect, the device 100 can be configured inside the automobile/vehicle, and can incorporate a display (such as 104) that can enable the web-based application 302 to be accessible and viewed by the user of the vehicle and view the medical parameters along with status of one or more HAS sensors. As shown, multiple HAG 202-1, 202-2, . . . , 202-*m*, can also be configured in the proposed architecture, wherein each HAG 202 can be configured to, as and when defined, transmit data from the HAS sensors to the web server 402.

According to one embodiment, application 302 that is hosted on the web server 402 can be accessed through establishment of a web socket 404 by means such as Hypertext Transfer Protocol (HTTP) or secured HTTP (HTTPS), or any other known configuration. In general, Web Sockets is a technology providing for two-way full-duplex communications channels, each over a single Transmission Control Protocol (TCP) socket, and designed to be implemented in web browsers and web servers. The current standard for Web Sockets is provided by The Web Socket protocol, Network Working Group of the Internet Engineering Task Force (IETF), Dec. 16, 2009. The HTTP protocol is intended as a request-response communication method where each request-response pair requires a web client (typically a web browser) to open a new socket to a web server, perform the communication and then shut down the socket. A common alternative to HTTP is to provide a secondary communication socket for high-speed data alongside the HTTP communication channel. Effectively, the web client communicates via HTTP for the presentation information, and via a separate dedicated socket for high-speed bi-directional data communication. Therefore, any means to enable any of the functional device 100 and/or the HAG 202 to access the web application 302 is completely within the scope of the present disclosure.

Figure 5A:
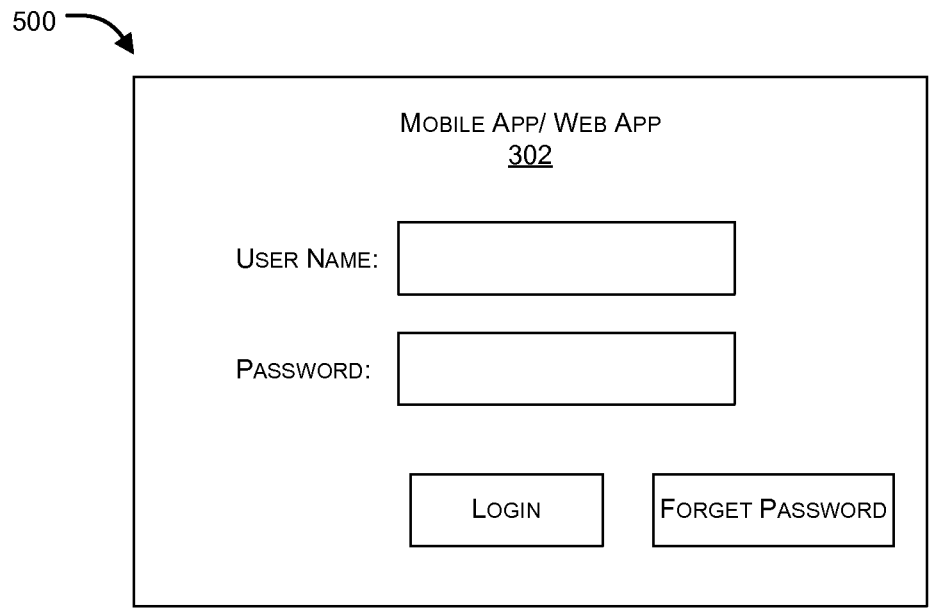
FIG. 5A illustrates an exemplary representation showing user interfaces of the proposed web application in accordance with an embodiment of the present disclosure.
Figure 5B:
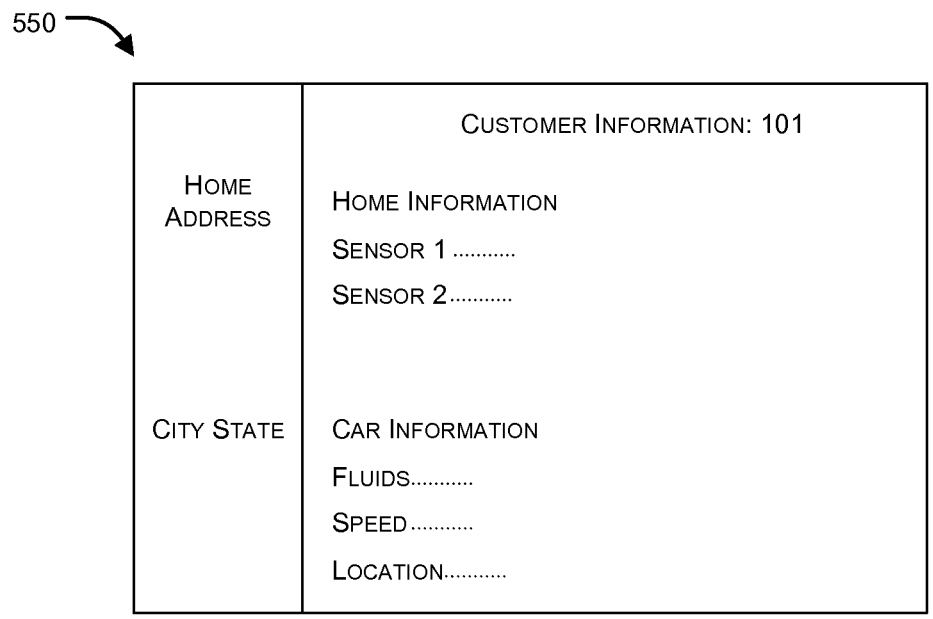
FIG. 5B illustrates an exemplary representation showing user interfaces of the proposed web application in accordance with an embodiment of the present disclosure.

FIGS. 5A and 5B illustrate an exemplary representations showing user interfaces of the proposed web application 302 in accordance with an embodiment of the present disclosure. In an aspect, the proposed web application 302 can be accessed on any computing device including but note limited to laptop, smart phones, mobile phones, tablet PCs', among other like devices, wherein the application can not only be used by users/occupants of the vehicles, but also be other stakeholders such as medical professionals or health centers, among others that can access health parameters and/or HAS sensor values. As shown in FIG. 5A, the web application 302 can provide an authentication means 304 that can expect each user, such as an occupant of a vehicle, to enter a username and password to login, and then access health parameter records, HAS data values from one or more sensors, among other information such as vehicle parameters/attributes, preferences/settings of the occupant among other like information. In addition, other users such as doctors or relatives/parents can also view health parameters and/or HAS information and make recommendations/suggestions/reminders that can be visible to the occupants of the vehicle.

As shown in FIG. 5B, interface of the web application 302 on a functional device 100 can include customer information, customer profile such as name, address, demographic details, preferences, psychographic details, health parameter values, HAS values, vehicle information, vehicle settings, among other like information, all of which is completely within the scope of the present disclosure.

Figure 6:
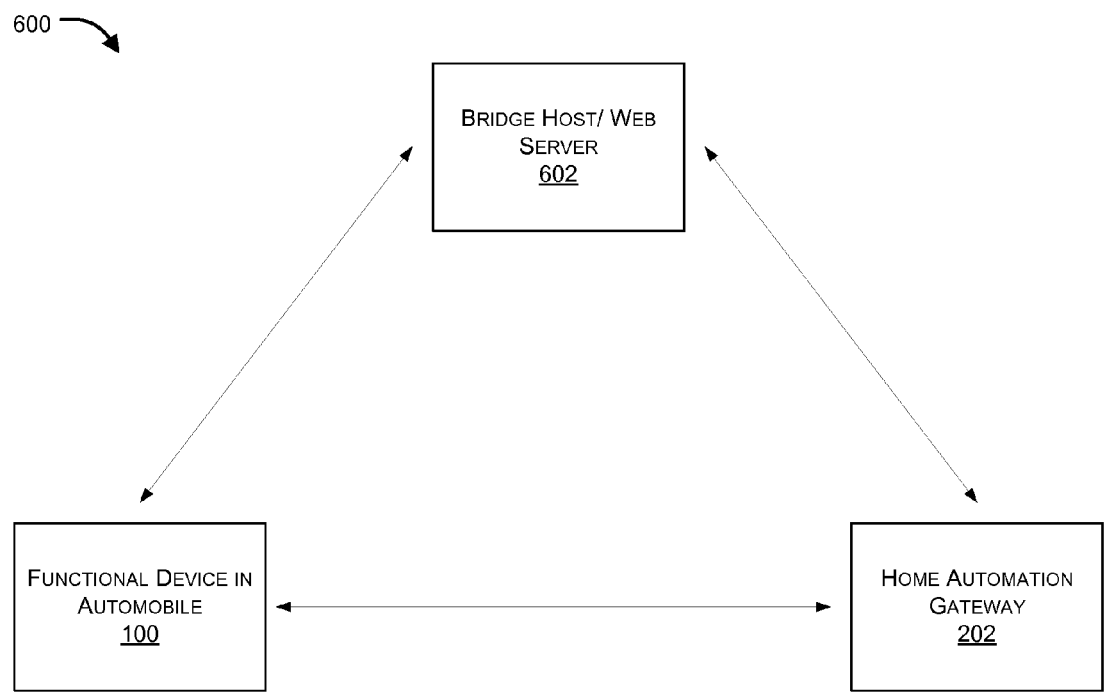
FIG. 6 illustrates an exemplary representation showing communication between a functional device and a HAG in accordance with an embodiment of the present disclosure.

FIG. 6 illustrates an exemplary representation 600 showing communication between a functional device 100 and a HAG 202 in accordance with an embodiment of the present disclosure. As shown, functional device 100 that is configured in an automobile can either be directly coupled with the HAG 202 through cellular or Internet connection and/or can be operatively coupled with the HAD 202 through a web server 602, which can enable access to HAS sensor data, viewing of status of devices connected with the HAS sensors, and controlling the operation of such devices.

In an aspect, as mentioned above, functional device 100 can include a user interface that enables the occupant of a vehicle to view the current status of the HAS sensors and control them though either the user interface, or through other means such as voice, gestures, among others. In case there is a direct connection between the device 100 and HAG 202, communication means such as SMS, voice based instructions, web-application based instructions, among other like mediums can be incorporated to enable controlling of the HAS devices such as doors, lights, fans, windows, air conditioners, among others. Data connection between the HAS 202 and the device 100 can be enabled using, for instance, web sockets or TCP/IP sockets.

In another aspect, in case communication between the device 100 and the HAG 202 is to take place through a web server such as 602 by means of a web application, a "receive info request" can first be received by the web server 602 in a web socket from the functional device 100, based on which the request can be processed and format translation/conversion, if necessary can be performed. The translated request can then be forwarded to the HAG 202 through a second web socket of the web server 602, wherein response from the HAG giving status/indication of one or more HAS sensors can be received at the second web socket of the server 602, and can then again be processed in the format compatible with the functional device 100. The processed response can then be relayed back to the functional device 100 through the first web socket to complete the communication transaction.

Figure 7:
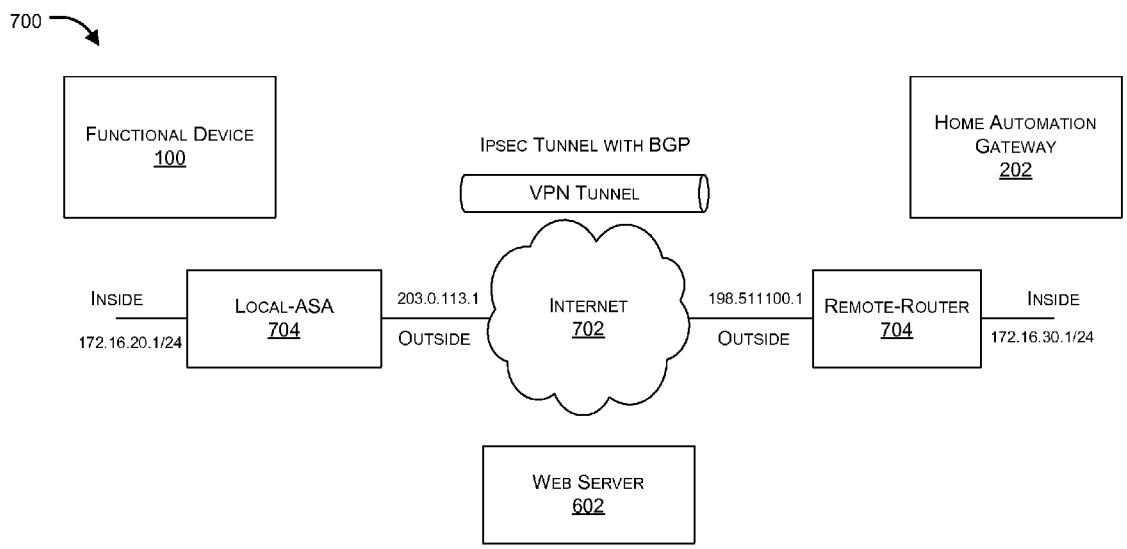
FIG. 7 illustrates another exemplary representation showing communication between a functional device and a HAG in accordance with an embodiment of the present disclosure.

FIG. 7 illustrates another exemplary representation 700 showing communication between a functional device 100 and a HAG 202 in accordance with an embodiment of the present disclosure. As shown device 100 can be operatively coupled through the Internet 702 with the HAG 202 by means of one or more network level devices such as routers, switches, hubs, application security appliance (ASA), gateway devices, among other like devices, collectively referred to as 704 hereinafter. Internet 702 can further be operatively coupled with web server such as 602 and host a web application using which health parameters, HAS sensor output values, vehicle occupant's profile, vehicle preferences/settings, can be stored, viewed, and customized.

According to one embodiment, the functional device 100 can directly interact with the HAG 202/remote home automation server through IPSEC VPN tunnel by looking up for the IP address of the other device from an IP table stored in the web server 602 or locally and requesting the data by connecting to that IP address directly. As mentioned above, by sending a SMS message to the cellular number of the HAG server 202, when the HAG 202 receives the SMS message, it automatically decodes the instructions and returns the response for the request by an SMS message. According to one embodiment, apart from IPSec, any other tunneling technologies such as MPLS, ATM/Frame Relay, IP-in-IP, GRE, L2TP, and GTP can be configured to enable tunnels. One skilled in the art will appreciate that this is not an exclusive listing of tunneling technology.

According to another embodiment, communication can also be established between the device 100 and HAG 202 by means of the web server of either the functional device 100 and/or of the HAG 202. Such a web server can be launched either from the CPU 102 of the functional device 100 or from the Wi-Fi module of any other component from within or outside the device (functional device 100 or HAG 202).

Figure 8:
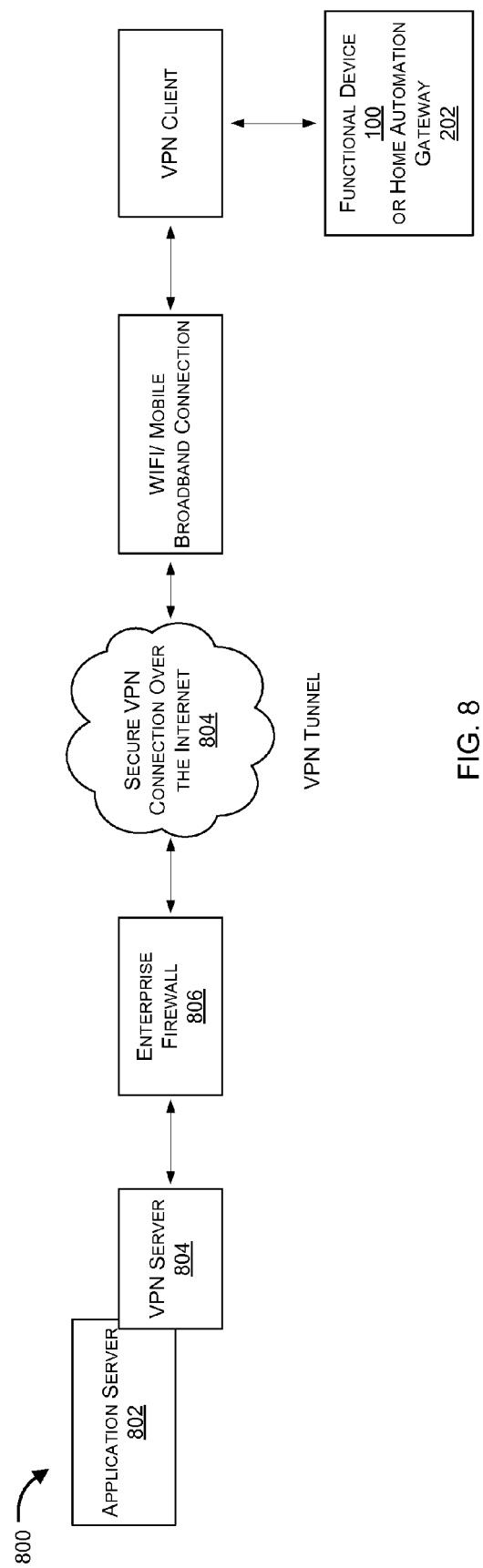
FIG. 8 illustrates an exemplary representation showing coupling between a functional device or HAG and an application server in accordance with an embodiment of the present disclosure.

FIG. 8 illustrates an exemplary representation showing coupling between a functional device 100 or HAG 202 and an application server 802 in accordance with an embodiment of the present disclosure. As can be seen, device 100/HAG 202 can be configured as Virtual Private Network (VPN) client device and can access the application server 802 by means of a secure VPN connection 804 over the Internet. The VPN connection 804 enables access to a VPN server 804 that is operatively coupled with the application server 802. Access to the VPN server 804 can be enabled by means of an enterprise firewall or any other suitable network security device 806. According to one embodiment, VPN client can be enabled to connect with the VPN server 804 through WiFi and/or mobile broadband connection or any other known connection means. According to one embodiment, VPN tunneling protocols can include point-to-point tunneling protocol (PPTP), layer two tunneling protocol (L2TP), and the like, wherein the HAG 202/functional device 100 can be configured in a form factor that is similar to other computing devices such as personal computer (PC), laptop, personal digital assistant (PDA), mobile phones, smart phones, tablet PC's, and the like While embodiments of the present invention have been illustrated and described, it will be clear that the invention is not limited to these embodiments only. Numerous modifications, changes, variations, substitutions, and equivalents will be apparent to those skilled in the art, without departing from the spirit and scope of the invention, as described in the claim.

What is claimed is:

1. A system, comprising:
   a functional device configured in an automobile, said functional device comprising one or more sensors that measure at least one health parameter of an occupant of the automobile, and further comprising a user interface;
   a home automation gateway (HAG), said HAG comprising one or more home automation systems (HAS) sensors placed inside a building; and
   a first computing device and a second computing device;
   wherein said functional device is configured to retrieve one or more automobile parameters and settings, wherein said functional device stores said at least one health parameter in real-time in secured form on the first computing device, wherein said functional device is further remotely coupled with the home automation gateway (HAG) in a manner that enables presentation of reading of the one or more home automation system (HAS) sensors on the user interface of said functional device, and wherein reading of the one or more home automation system (HAS) sensors are stored in real time by said HAG in secured form on the second computing device,
   wherein said functional device is further configured to enable the occupant of the automobile to, upon authorization, control any or combination of said one or more automobile parameters and settings, said at least one health parameter through the user interface, and one or more HAS sensors,
   wherein said functional device accesses said health parameters and reading of said one or more home automation system (HAS) sensors by a web application that is configured on a web server, and
   wherein said functional device is connected with said HAG by a Virtual Private Network (VPN) connection.

2. The system of claim 1, wherein said first computing device and said second computing device are same.

3. The system of claim 1, wherein said functional device is directly connected with said HAG.

4. The system of claim 1, wherein said functional device is connected with said HAG by a third computing device.

5. The system of claim 4, wherein said third computing device is any of said first computing device and said second computing device.

6. The system of claim 4, wherein at least one of said functional device and said HAG is connected with said third computing device by a network security device.

* * * * *